United States Patent [19]

Nosco

[11] Patent Number: 5,419,905
[45] Date of Patent: May 30, 1995

[54] TECHNETIUM-99M COMPLEXES FOR USE AS RADIOPHARMACEUTICALS

[75] Inventor: Dennis L. Nosco, Florissant, Mo.

[73] Assignee: Mallinckrodt Medical, Inc., St. Louis, Mo.

[21] Appl. No.: 855,256

[22] Filed: Mar. 23, 1992

Related U.S. Application Data

[62] Division of Ser. No. 605,207, Oct. 29, 1990, Pat. No. 5,116,598.

[51] Int. Cl.$^6$ ............................................. A61K 49/02
[52] U.S. Cl. ................................. 424/1.65; 562/561; 562/565
[58] Field of Search ...................... 424/1.1; 534/10, 14; 562/561, 565; 564/253, 256, 268

[56] References Cited

U.S. PATENT DOCUMENTS

| | | | |
|---|---|---|---|
| 4,615,876 | 10/1986 | Troutner et al. | 424/1.1 |
| 4,789,736 | 12/1988 | Canning et al. | 534/14 |
| 4,818,813 | 4/1989 | Nowotnik et al. | 534/14 |

OTHER PUBLICATIONS

Chemical Abstract 116(24):245168c, Nov. 27, 1991.

*Primary Examiner*—Gary Geist
*Assistant Examiner*—Lara E. Chapman
*Attorney, Agent, or Firm*—David A. Hey; Brian K. Stierwalt; Thomas P. McBride

[57] ABSTRACT

The present invention relates to novel technetium-99m complexes and to methods of preparing the complexes. The present invention further relates to a radiopharmaceutical compositions comprising the complexes, to the use of the compositions for examining the renal function, and to a kit for preparing such compositions.

15 Claims, No Drawings

TECHNETIUM-99M COMPLEXES FOR USE AS RADIOPHARMACEUTICALS

This is a division of application Ser. No. 07/605,207 filed Oct. 29, 1990, now U.S. Pat. No. 5,116,598.

The present invention relates to a technetium-99m complex and to a method of preparing the complex. The present invention further relates to a radiopharmaceutical composition comprising the complex, to the use of the composition for examining the renal function, and to a kit for preparing such a composition.

Radioactive labelled compounds are used for the examinations of patients, for example, into deviations in shape and function of internal organs and into the presence and location of pathological processes in the body. For this purpose, a composition in which the radioactive compound is present is administered to the patient, for example, in the form of an injectable liquid. By means of suitable detection apparatus, e.g. a gamma camera, images can be obtained of, for example, the organ or the pathological process in which the radioactive compound has been incorporated, by recording the emitted radiation. Compounds which are generally used for examining the renal function are radioactive Tc-99m MAG$_3$, iodo-Hippuran ® and Tc99m-diethylene triamine pentaacetic acid (DTPA), which will be discussed hereinafter.

In addition to the passive glomerular filtration, an active tubular secretion also takes place in the kidneys. The functioning of the kidneys is determined to a considerable extent by this active filtration. In an adult person approximately 125 ml of blood plasma per minute is purified by glomerular filtration. This means that the clearance is 125 ml per minute. The total clearance which can be effected by the kidneys is 600 to 700 ml of plasma per minute. It appears that the above-mentioned chelate of DTPA clears from the kidneys at a rate of 100 ml of blood plasma per minute, and therefore the chelate is eliminated entirely or substantially entirely by glomerular filtration and hence is not very suitable for examining the renal function.

There exists a great need for a suitable composition for examining the renal function which is permanently available, in particular for kidney transplantation patients, accident victims and patients after large vascular operations.

An example of a radioactive iodo-Hippuran ® compound generally used for examining the renal function is iodo-131-Hippuran ®, which is secreted actively tubularly and hence is very suitable for examining the renal function as regards organ specificity. Further, iodo-131-Hippuran ® is excellently suitable for the above applications, because of its ready availability. However, like all iodo-131 compounds, iodo-131-Hippuran ® constitutes a serious radiation burden for the patient. Therefore, iodo-131 compounds can be administered to the patient only in restricted doses, as a result of which the resulting information is insufficient to obtain statistically reliable images of the renal function by means of a gamma camera.

Another radioactive iodo-Hippuran ® compound frequently used for examining the renal function is iodo-123-Hippuran ® which is excellently suitable as regards organ specificity and restricted radiation burden. Iodo-123-containing compositions, however, have only a restricted availability due to the short half-life, i.e. 13.3 hours, and because the production of iodo-123 must necessarily be carried out in a cyclotron.

Technetium-99m complexes which show a tubular secretion which is comparable to that of iodo-Hippuran ® are known from European Patent Application 173424. This application discloses the preparation of Tc-99m-mercaptoacetyltriglycine (Tc99m-MAG3), which complex is secreted by the kidneys selectively and approximately equally rapidly to iodo-Hippuran ®. However, the organ specificity of said complexes still leaves something to be desired. This is a disadvantage, especially when these compounds are used for function examination. Chemically related compounds having an improved organ specificity are the subject of the recently published European patent application 250013.

In connection with the comparatively short half-life of radionuclides it is often nearly impossible to deliver the ready-to-use labelled product to the user. In such cases it is desirable to place the various reaction components at the user's disposal in a so-called kit. By means of this kit, the user himself can carry out the labelling reaction with the radionuclide in the clinical hospital or laboratory at any desired moment. This is favorable in particular for preparing technetium-99m-labelled products, because most modern clinical hospitals or laboratories have at their disposal a molybdenum-technetium generator, from which the desired quantity of technetium-99m can very easily be obtained in the form of a pertechnetate solution. The process of preparing the technetium-99m-labelled product from the supplied kit must be able to be carried out by the user with a few simple manipulations, without laborious operations, and by using the facilities which are at his disposition in the clinic. Furthermore, the stability of the labelled product is of great importance. In fact, if the stability is not satisfactory, there is insufficient opportunity to be able to prepare and perform the renal function examination in patients carefully. Moreover, there is a constant risk that if the shelf life is exceeded, a contaminated composition may be administered to the patient and the results of the examination will no longer be reliable.

It has now been found that the shelf life of technetium-99m complexes described in the European patent applications mentioned hereinbefore is at most a few hours, depending on the complex-forming ligands and the labelling method used. In practice this is often insufficient because it is desired to have a suitable composition available immediately at any instant of the day. Moreover, it is advantageous that a radioactive composition need be prepared only once daily. Furthermore the reaction conditions in which the user has to prepare the labelled product from the kit are not very favorable. In fact, in order to prepare the technetium-99m complexes described in the European patent applications, the kit constituents must be heated for at least 5 minutes with the eluate from a molybdenum-technetium generator on a boiling water bath to produce the desired reaction resulting in the formation of the technetium-99m complex. In carrying out this operation, the possibility of accidents in which radioactive material is released are very possible.

It is one object of the present invention to provide a technetium-99m complex suitable for examining the renal function which complex has a high organ specificity and an improved stability, and which is better suitable for the preparation from a kit than the above known complexes.

The objects of the present invention can be achieved, according to one embodiment of the present invention, by providing a technetium-99m complex which satisfies the general formula:

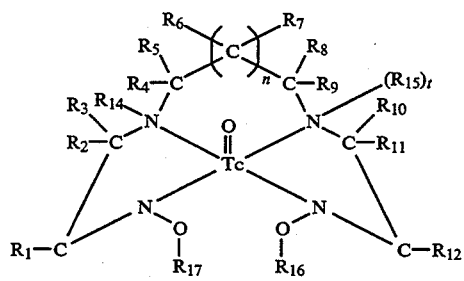
(I)

wherein
each of the symbols $R_1$–$R_{15}$ is individually selected from the group consisting of hydrogen, straight or branched, unsubstituted or substituted alkyl having 1–4 carbon atoms, and ACOOH, wherein A is a straight or branched, unsubstituted or substituted alkyl group having 0–4 carbon atoms;

$R_4$ together with $R_5$ or $R_8$ together with $R_9$ additionally may form an oxygen atom;

each of the symbols $R_{16}$ and $R_{17}$ is individually selected from the group consisting of alkyl, hydroxy substituted alkyl, or hydrogen;

Tc represents technetium-99m;
t is 0 or 1; and
n is 0 or 1;
with the provisos that
(a) if $R_{14}$, and/or $R_{15}$ are/is ACOOH, then A is a straight or branched, unsubstituted or substituted alkyl group having 1–4 carbon atoms;
(b) at least one of the symbols $R_1$–$R_{15}$ is ACOOH;
(c) at most four of the symbols $R_1$–$R_{15}$ are ACOOH; and
(d) if t is 1, at least two of the symbols $R_1$–$R_{15}$ are ACOOH;
or a pharmaceutically acceptable salt of this compound.

When the above symbol t is 1, there is a coordinative bond between the amino-N and Tc. The coordinative bond in the above formula (I) also exists where N-$R_{14}$ has been exchanged with N-$(R_{15})_t$.

The objects of the present invention can also be achieved by providing a technetium-99m complex which satisfies the general formula:

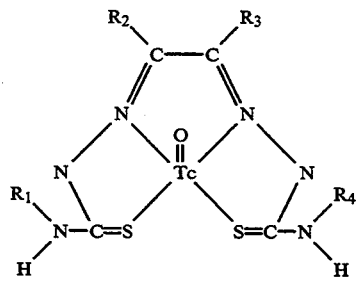
(II)

wherein
each of the symbols $R_1$–$R_4$ are defined in the same manner as above in formula (1); and
Tc represents technetium-99m;
with the provisos that
(a) at least one of the symbols $R_1$–$R_4$ is ACOOH; and
(b) at most four of the symbols $R_1$–$R_4$ are ACOOH;
or a pharmaceutically acceptable salt of this compound.

A further embodiment of the present invention achieves the above objects by providing a technetium-99m complex which satisfies the general formula:

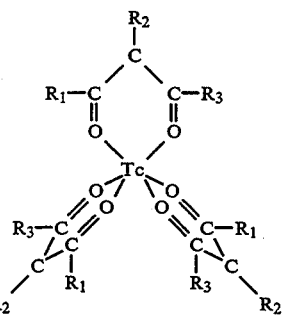
(III)

wherein
each of the symbols $R_1$–$R_3$ are defined in the same manner as above in formula (I); and
Tc represents technetium-99m;
with the provisos that
(a) at least one of the symbols $R_1$–$R_3$ is ACOOH; and
(b) at most three of the symbols $R_1$–$R_3$ are ACOOH;
or a pharmaceutically acceptable salt of this compound.

If the above symbols $R_1$–$R_{15}$ represents or include substituted alkyl groups, such substituents are preferably selected from hydroxy groups and acid groups; wherein examples of suitable acid groups are carboxy groups.

Pharmaceutically acceptable salts may be salts with various acids, for example, hydrochloric acid, sulfuric acid, phosphoric acid, perchloric acid or organic acids such as citric acid, tartaric acid, and the like.

The technetium-99m complexes according to the present invention may occur in stereoisomeric configurations which may differ in the biological properties. In these cases, starting from the stereochemically most suitable complex-forming ligands, stereoisomeric technetium complexes can be prepared having properties which are most favorable for the intended purpose.

A technetium-99m complex according to the present invention is generally used in the form of a composition which is suitable for examining the renal function. In which is suitable for examining the renal function. In addition to the radioactive complex, such a radiopharmaceutical composition will usually comprise a liquid, pharmaceutically acceptable carrier material, preferably a physiological saline solution. A radiodiagnostic examination can be performed with such a composition by administering the composition to a warm-blooded living being, in particular a primate, in a quantity of 0.1 to 30 mCi, preferably of 0.5 to 10 mCi, per 70 kg of body weight, and by then recording the radioactive radiation emitted by the living being by means of, for example, a gamma camera.

The present invention further relates to a method of preparing a technetium-99m complex according to the present invention by reacting technetium-99m in the form of a pertechnetate in the presence of a reducing agent and optionally a suitable chelator with an appropriate compound. In particular, when it is desired to form a technetium-99m complex according to formula (I) above, then the appropriate compound should satisfy the general formula:

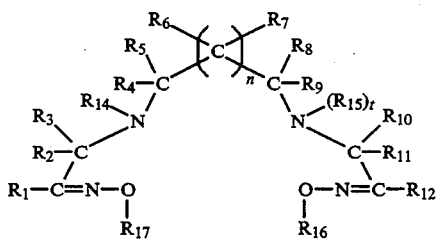

(IV)

wherein
the symbols n, $R_1$–$R_{15}$, and $R_{16}$–$R_{17}$ have the meanings give above in formula (I).

Further, when it is desired to form a technetium-99m complex according to formula (II) above, then the appropriate compound should satisfy the general formula:

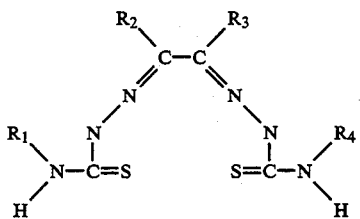

(V)

wherein
the symbols $R_1$–$R_4$ have the meanings given above in formula (II).

In addition, when it is desired to form a technetium-99m complex according to formula (III) above, then the appropriate compound should satisfy the general formula:

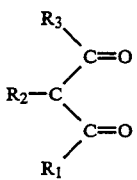

(VI)

wherein
the symbols $R_1$–$R_4$ have the meanings given above in formula (III).

It should be noted that when using the compound according to formula (VI) above, three such compounds bond with all six coordination sites of the technetium-99m in order to six coordination sites of the technetium-99m in order to form the complex according to formula (III) above.

Examples of suitable protective groups Y for each of the formulas (IV), (V), and (VI) above, are acetyl, trifluoroacetyl, hydroxacetyl, carboxyacetyl, acetamidomethyl, benzoyl, benzyl, benzoyl-aminomethyl and the like.

The reducing agent serves to reduce the Tc-99m pertechnetate which in a physiological saline solution is eluted from a molybdenum-technetium generator. Suitable reducing agents are, for example, dithionite, formamidine sulphinic acid, diaminoethane disulphinate or suitable metallic reducing agents such as Sn(II), Fe(II), Cu(I), Ti(III) or Sb(III); wherein Sn(II) has proved to be particularly suitable.

For the above-mentioned complex-forming reaction, technetium-99m is reacted with the above-mentioned compounds according to formulas (IV), (V), or (VI), as a salt or in the form of technetium bound to comparatively weak chelators. In the latter case the desired technetium-99m complex is formed by ligand exchange. Examples of suitable chelators for the radionuclide are dicarboxylic acids, polycarboxylic acids or hydroxy carboxylic acids, such as oxalic acid, malonic acid, succinic acid, maleic acid, orthophthalic acid, malic acid, lactic acid, tartaric acid, citric acid, ascorbic acid, salicyclic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because it appears that a chelate or technetium-99m with one of these chelators undergoes the desired ligand exchange particularly easily.

Since the radiopharmaceutical composition according to the present invention can be prepared so easily and simply, the preparation can be carried out readily by the user himself. Therefore, the present invention also relates to a so-called kit, comprising:

(1) A compound according to one of the general formulas (IV), (V), or (VI); the compound optionally being in a dry condition, and also optionally having an inert, pharmaceutically acceptable carrier and/or auxiliary substances added thereto; and (2) a reducing agent and optionally a chelator; wherein ingredients (1) and (2) may optionally be combined; and further wherein instructions for use with a prescription for carrying out the above-described method by reacting ingredients (1) and (2) with technetium-99m in the form of a pertechnetate solution may be optionally included.

Examples of suitable reducing agents and chelators for the above kit have been listed above. The pertechnetate solution can be obtained simply by the user himself from a molybdenum-technetium generator which is available to him. As noted above the ingredients (1) and (2) may be combined, provided they are compatible. Such a monocomponent kit, in which the combined ingredients are preferably lyophilized, is excellently suitable to be reacted by the user with the pertechnetate solution in a simple manner.

The ingredient (1) of the above kits may be delivered as a solution, for example, in the form of a physiological saline solution, or in some buffer solution, but is preferably present in a dry condition, for example in a lyophilized condition. When used as a component for an injection liquid, it should be sterile, and, if the ingredient (1) is present in a dry condition, the user should use a sterile physiological saline solution as a solvent. If desired, ingredient (1) may be stabilized in a usual manner with suitable stabilizers such as ascorbic acid, gentisic acid or salts of these acids, or it may be provided with other auxiliary means such as fillers, e.g. glucose, lactose, mannitol, inositol, and the like.

The stereochemical configuration of the technetium-99m complex is determined by the configuration of the starting compound of the above general formulas (IV), (V), or (VI). Different stereoisomers of these compounds can be separated from each other by using techniques known for this purpose such as recrystallization and/or chromatographic methods. If desired, for the separation the stereoisomers mixture may be converted with a stereochemically pure D- or L-isomer of a suitable amine, carboxylic acid, and the like, after which the isomer separation is carried out, succeeded by eliminating the used amine, carboxylic acid, etc. An alternative, also particularly suitable method of preparing stereochemically pure compounds according to general formulas (IV), (V), or (VI), consists in using for the synthesis a starting material which is already stereochemically pure and which is easily available or obtainable as a stereoisomer, and in ensuring that during the synthesis of the intended compound, that the stereochemical purity is not lost, i.e. that no racemization occurs.

The foregoing has been a description of certain preferred embodiments of the present invention, but is not intended to limit the invention in any way. Rather, many modifications, variations and changes in details may be made within the scope of the present invention.

What is claimed is:

1. A compound useful in forming radiopharmaceutical complexes, said compound comprising a ligand having the formula:

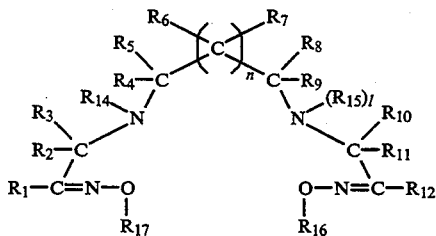

wherein
each of the symbols $R_1$–$R_{15}$ is individually selected from the group consisting of hydrogen straight or branched, unsubstituted or hydroxy or carboxy substituted alkyl having 1–4 carbon atoms, and ACOOH, wherein A is a straight or branched, unsubstituted or hydroxy or carboxy substituted alkyl group having 0–4 carbon atoms;

$R_4$ together with $R_5$ or $R_8$ together with $R_9$ additionally may form an oxygen atom;

each of the symbols $R_{16}$ and $R_{17}$ is individually selected from the group consisting of alkyl, hydroxy substituted alkyl, and hydrogen;

t is 0 or 1; and n is 0 or 1; with the provisos that (a) if $R_{14}$, and/or $R_{15}$ are/is ACOOH, then A is a straight or branched, unsubstituted or hydroxy or carboxy substituted alkyl group having 1–4 carbon atoms;

(b) at least one of the symbols $R_1$–$R_{15}$ is ACOOH;

(c) at most of four of the symbols $R_1$–$R_{15}$ are ACOOH; and (d) if t is 1, at least two of the symbols $R_1$–$R_{15}$ are ACOOH.

2. A kit for forming a radiopharmaceutical complex comprising:
a ligand having the general formula:

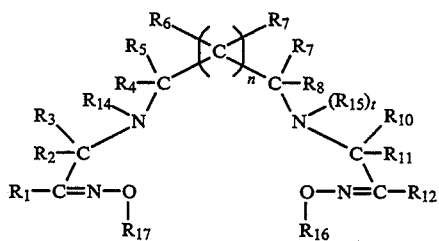

wherein
each of the symbols $R_1$–$R_{15}$ is individually selected from the group consisting of hydrogen, straight or branched, unsubstituted or hydroxy or carboxy substituted alkyl having 1–4 carbon atoms, and ACOOH, wherein A is a straight or branched, unsubstituted or hydroxy or carboxy substituted alkyl group having 0–4 carbon atoms;

$R_4$ together with $R_5$ or $R_8$ together with $R_9$ additionally may form an oxygen atom;

each of the symbols $R_{16}$ and $R_{17}$ is individually selected from the group consisting of alkyl, hydroxy substituted alkyl, and hydrogen;

t is 0 or 1; and n is 0 or 1; with the provisos that (a) if $R_{14}$, and/or $R_{15}$ are/is ACOOH, then A is a straight or branched, unsubstituted or hydroxy or carboxy substituted alkyl group having 1–4 carbon atoms;

(b) at least one of the symbols $R_1$–$R_{15}$ is ACOOH;

(c) at most four of the symbols $R_1$–$R_{15}$ are ACOOH; and (d) if t is 1, at least two of the symbols $R_1$–$R_{15}$ are ACOOH;

and further comprising a reducing agent.

3. A kit according to claim 2, wherein said reducing agent is selected from the group consisting of dithionite, formamidine sulphinic acid, diaminoethane disulphinate and a metallic reducing agent.

4. A kit according to claim 2, further including a pharmaceutically acceptable carrier.

5. A kit according to claim 4, wherein said carrier is a sterile physiological saline solution.

6. A kit according to claim 2, further including stabilizers and fillers.

7. A kit according to claim 6, wherein said stabilizers are ascorbic acid, gentisic acid or salts of these acids.

8. A kit according to claim 6, wherein said fillers are glucose, lactose, mannitol, inositol.

9. A kit according to claim 2, further including a chelator.

10. A kit according to claim 9, wherein said chelator is selected from the group consisting of dicarboxylic acids, polycarboxylic acids, hydroxy carboxylic acids, phosphorus compounds, and enolates.

11. A kit according to claim 2, further including instructions for use with a prescription for reacting the components of said kit with a radionuclide solution.

12. A kit according to claim 2, wherein said ligand and said reducing agent are combined, and are provided in a lyophilized condition.

13. The kit according to claim 3, wherein said metallic reducing agent is selected from the group consisting of An(II), Fe(II), Cu(I), Ti(III) and Sb(III).

14. The kit according to claim 10, wherein said dicarboxylic acid, polycarboxylic acid, or hydroxy carboxylic acid is selected from the group consisting of oxalic acid, malonic acid, succinic acid, maleic acid, orthophthalic acid, malic acid, lactic acid, tartaric acid, citric acid, ascorbic acid, salicyclic acid and glucoheptonic acid.

15. The kit according to claim 10, wherein said phosphorous compound is pyrophosphate.

* * * * *